United States Patent [19]

Münch et al.

[11] Patent Number: 4,935,031
[45] Date of Patent: Jun. 19, 1990

[54] PROCESS FOR SHORT-TERM PRESERVATION OF RAWHIDES AND SKINS

[75] Inventors: Norbert Münch, Kelkheim; Karlheinz Fuchs, Hünfelden, both of Fed. Rep. of Germany

[73] Assignee: Hoechst Aktiengesellschaft, Frankfurt, Fed. Rep. of Germany

[21] Appl. No.: 198,466

[22] Filed: May 25, 1988

[30] Foreign Application Priority Data

May 27, 1987 [DE] Fed. Rep. of Germany ....... 3717829

[51] Int. Cl.$^5$ .............................................. C14C 1/00
[52] U.S. Cl. ...................................... 8/94.18; 8/94.15
[58] Field of Search ............................. 8/94.15, 94.18

[56] References Cited

U.S. PATENT DOCUMENTS 1,927,910  9/1933  Balle et al. ........................... 8/94.18
3,885,910  5/1975  Fischer et al. ....................... 8/94.15

Primary Examiner—A. Lionel Clingman
Assistant Examiner—John F. McNally

[57] ABSTRACT

The process for the short-term preservation of rawhides and skins with an alkali metal chlorite solution which additionally also contains a compound of the formula 1

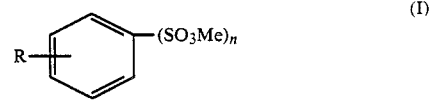

in which R denotes hydrogen or $C_1$–$C_{12}$-alkyl, Me denotes hydrogen or an alkali metal atom and n denotes 1 or 2. Because of their hydrotropic action, the addition of these compounds improves uniform penetration of the preservation solution into the hide.

13 Claims, No Drawings

PROCESS FOR SHORT-TERM PRESERVATION OF RAWHIDES AND SKINS

DESCRIPTION

Process for short-term preservation of rawhides and skins

The invention relates to an improved process for preserving rawhides and skins, in particular for protection from microorganisms. The process can be applied immediately after stripping the hides for short-term preservation or, in combination with known processes, also for permanent preservation.

The freshly stripped animal hides are processed immediately by leather factories only in exceptional cases. At normal temperature, however, the rawhides, which contain a large quantity of water, start to rot, since they are an ideal nutrient medium for microorganisms. Irreparable damage which renders them largely unsuitable for leather production is the result.

The freshly stripped skin must be rendered storable, that is to say preserved, in order to avoid such damage by rotting. Various processes which are said to effect destruction or reduction of the bacteria on the hide and provision of living conditions adverse to bacteria are known for this.

Many of the known processes are used both for short-term preservation and for long-term preservation. The result is that these processes are often uneconomical for only short-term preservation, since the work expended and the use of chemicals are usually the same in both cases.

The oldest and most used preservation process is treatment of the rawhides with salt (sodium chloride) or brine. The salt reduces the water content of the hide from about 65% to 35-40% and thus provides a living atmosphere which is adverse to bacteria, so that bacteria growth is inhibited.

Concentrated salt solutions moreover also have a certain bactericidal action. A very large quantity of salt is consumed for this type of preservation, 30-60% by weight, based on the green weight of the hides, being needed, depending on the effect sought. The salt content of the effluent of the rawhide store and leather factories is thereby increased to the extent that ecological efforts and requirements are no longer fulfilled.

It is therefore also known that the rot-preventing effect of the salt can be increased by additions of biocidal or bactericidal agents, with a simultaneous reduction in the amount of salt. The most diverse chemical substances have been used as additives, such as, for example, naphthalene, p-chloro-m-cresol, sodium silicofluoride, organotin compounds, chlorinated phenols, pyridine derivatives, quaternary ammonium compounds, zinc salts, monochloroacetic acid and many others. Chemicals which have no pronounced bactericidal action, but are said to intensify the growth-inhibiting action of the salt, have also been used as additives. Sodium sulfate, sodium bisulfate, alkali metal perborates, sodium sulfite, sodium carbonate and alum may be mentioned here.

However, all these additives still necessitate a relatively high quantity of salt, disposal of which is difficult. After such preservation, the waste obtained in the course of leather production, in particular the leather scraps for glue, can furthermore be used only with reservation for processing of, for example, protein-containing feedstuffs.

There has therefore been no lack of attempts to develop salt-free preservation processes. Such processes are described below, in order to illustrate the diversity of the methods.

1. Preservation by drying

This process is usually applied in tropical countries. Severe damage to the hide can arise due to intense solar radiation or inadequate ventilation during drying. Since a bacterial attack on the hide material also already takes place during drying, these hides usually have significant quality deficiency.

2. Preservation by solvent dehydration

Water-miscible solvents, such as, for example, dimethylsulfoxide, have been proposed for dehydrating the hides. These methods are expensive in terms of apparatus and are unacceptable and uneconomical for toxicological and safety reasons.

3. Preservation by treatment of the hides with solutions of bactericides

Good preservation can in many cases be achieved by spraying or bath treatment with solutions containing 0.5-1.0% of bactericidally active substances, but the effect usually lasts for only a few days and is uneconomical because of the relatively high costs of bactericides and the adverse influence on utilization of the scrap leather for glue.

Pauckner and co-workers (Leder- und Häutemarkt 80, 5, page 86) have also found that in the chrome-tanned state, the leather produced from such rawhides usually has a greyish-tinged color and is speckled in the folds.

4. Preservation by irradiation

Preservation of rawhides by irradiation with ionic or electron beams has recently also been proposed. The expenditure on such a process, the effectiveness of which is moreover in dispute, does not allow widespread use in practice.

5. Preservation by cooling

Storing of rawhides in cold stores at temperatures of about 5° C. is particularly suitable for short-term preservation of the rawhides. However, the process is extremely costly because of the provision of sufficiently large low temperature capacities.

6. Preservation by treatment of the hides with sodium chlorite

Experiments on preservation by immersion or spraying of the rawhides with sodium chlorite solutions have been carried out in South Africa (see LIRI Report 433, September 1983). The results obtained by the LIRI Institute in Grahamstown showed the first signs of rotting on the rawhide only after about 8 days following treatment with 1% of a 30% strength sodium chlorite solution (percentage data based on the hide weight) and at a storage temperature of 25° C.

However, Na pentachlorophenolate was always used in these experiments. The results are interesting, but the period of preservation still does not seem to be satisfactory and the use of Na pentachlorophenolate is unacceptable for toxicological reasons.

In similar experiments carried out by the CSIRO Institute in Melbourne (JALCA, Vol. LXV, No. 2, February 1970, page 44 et seq.), the first signs of rotting appeared after 6 days following spraying of the rawhides and at a storage temperature of 25° C., whilst after bath preservation with 2.7% of a 30% strength sodium chlorite solution (percentage data based on the hide weight), the hides could be stored for about 10 days at 25° C. before the first bacterial damage occurred In the case of spray treatment, the time of 6 days is so short that under normal circumstances it is not sufficient for the necessary working before delivery to the leather factories.

The bath preservation here was also carried out with an addition of bactericides, which is unacceptable for the above reasons.

All the processes so far described for preserving rawhides, in particular both for long-term and for short-term preservation have deficiencies which make the development of an effective but nevertheless economical and toxicologically and ecologically acceptable preservation method urgent.

The continuing trend of passing the rawhides obtained in slaughter houses to the leather factories for processing after only a short period of storage demands above all effective short-term preservation. Although protection lasting only a few days is also of importance, since the rawhides can already suffer significant damage in the short time between stripping and further transportation for storage or to leather factories, medium-term preservation for 2-3 weeks is nevertheless desirable. Reliable protection should thereby also be guaranteed for the period of collection, transportation, sorting and delivery to leather factories.

The object of the invention was therefore to improve the short-term preservation of fresh animal hides and skins in order to achieve preservation for 2-3 weeks with reduced pollution of the effluent and adaptation to the increased toxicological and ecological requirements and under economically acceptable conditions.

It has now been found that this aim can be achieved if the rawhides and skins are treated not with Na chlorite by itself but additionally also with a hydrotropic compound in the form of alkylphenyl-mono- or -disulfonic acids or salts thereof.

The subject of the invention is thus a process for, in particular, short-term preservation of rawhides and skins with an alkali metal chlorite solution, in particular with Na chlorite, wherein a compound of the formula

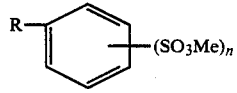

in which R denotes hydrogen or $C_1$-$C_{12}$-alkyl, Me denotes hydrogen or an alkali metal atom and n denotes 1 or 2, is additionally also used in the chlorite solution. The Na salt of m-benzene-disulfonic acid is preferred.

Because of their hydrotropic action, the additives improve uniform penetration of the preservation solution into the hide and in addition increase the depth of penetration. An increased protection of the preserved hide from bacteria is in this way provided and manifests itself in a longer storage time before rotting occurs.

The addition of wetting agents and emulsifiers, such as, for example, oxyethylated alkylphenols, alkylphenolethers, sulfonic acid esters of oxyethylated fatty acids or fatty alcohols, oxyethylated fatty amines or polyglycol ethers, and of emulsifiers, such as, for example, salts of $C_8$-$C_{19}$-fatty acids with alkali metals, ammonia or amines, salts of fatty alcohol sulfuric acid esters, sulfuric acid esters of oxyethylated fatty alcohols, Na salts of dialkylsulfosuccinates, naphthalenesulfonates and alkylnaphthalenesulfonates, intensify the effect of the hydrotropic substances mentioned.

Additions of polyphosphates and alkali metal salts of nitrilotriacetic acid and ethylenediaminetetraacetic acid have moreover proved suitable for intensifying the preserving effect.

The hydrotropic substances of the above formula are added to the sodium chlorite solution in amounts of 0.5 to 10%, preferably 3-5% (the percentage data relate to the amount of sodium chlorite solution used). The concentration of the Na chlorite solution used is 10-50%, preferably 30% by weight. The additions of wetting agents and/or emulsifiers are 0.1-5%, preferably 0.5-1%, also based on the sodium chlorite solution of the stated concentration.

The preservation can be carried out either by a spray process or in a bath treatment, for example in a vat, in a mixer or in a paddle. In the case of preservation by spraying, 5 to 10 ml per 0.1 $m^2$ of an aqueous solution containing 150-200 g of sodium chlorite, 15-30 g of hydrotropic substance of the above formula, 1-5 g of wetting agent and 0.1-0.5 g of fungicide per liter of liquor are sprayed onto the grain and flesh side of freshly stripped cattle hides. In bath preservation, the hides are treated in an aqueous liquor containing 10-30% by weight of a 10-50% strength sodium chlorite solution, 0.5-5% by weight of hydrotropic auxiliary of the abovementioned formula, 0.5-3% by weight of wetting agent and 0.05-0.5% by weight of fungicide, depending on the apparatus used.

The superiority of the present invention manifests itself in particular in preservation by spraying, since the preservation solution which is applied only to the surface in this process is distributed more uniformly and more quickly over the entire surface of the hide by the additives according to the invention and penetrates more deeply into the hide. The same effect is achieved to an even greater degree in bath preservation.

The rawhides and skins preserved according to the present invention have, depending on the concentrations used and the storage temperature, a resistance to bacterial damage and rotting of 2-3 weeks, a period which under normal circumstances is sufficient to bring the hides from the slaughter house via the collection point, with transportation and sorting, to the leather factory. Since the preservation solution mentioned does not have a fungicidal action, the addition of a suitable fungicide, for example chloroacetamide, is advisable for an envisaged storage of more than two weeks or for storage at temperatures significantly above 20° C.

The process of the invention can also be used for longterm preservation if salt preservation is carried out after the treatment with the solutions mentioned according to the invention. In such cases, the amount of salt can be significantly reduced, depending on the envisaged storage time and storage temperature, and the pollution of the effluent can thereby be reduced.

It has also been found that the hides and skins treated with the preservation solutions mentioned according to the invention offer further distinct advantages during processing to leather. The removal of the hair in lime and lime paste proceeds more quickly and with less base material, as does the removal of the epidermis. Cleaner pelts are therefore obtained than, for example, with salt preservation.

The following Examples serve to illustrate the invention in more detail.

EXAMPLE 1

100 kg of freshly stripped cattle hides are sprayed to saturation on the flesh and hair side with a solution consisting of:

260 parts by weight of water
700 parts by weight of 30% strength sodium chlorite solution
35 parts by weight of Na m-benzene-disulfonate
5 parts by weight of nonylphenol with 8 mol of ethylene oxide and
0.5 part by weight of chloroacetamide The hides treated in this way are stored at 25° C. After 2 weeks, the hides looked very clean, had a fresh smell and showed no hair slippiness.

EXAMPLE 2

100kg of freshly stripped cattle hides are placed in a bath of the following composition:

400% of water
20% of 30% strength sodium chlorite solution
0.6% of Na m-benzene-disulfonate
0.4% of sodium tripolyphosphate
1.5% of Na laurylsulfate
0.05% of chloroacetamide The percentage data relate to the rawhide weight. The hides are left in the bath. At a storage temperature of 25° C., even after 4 weeks, no signs of hair slippiness or rotting had yet occurred.

EXAMPLE 3

100 kg of freshly stripped cattle hides are milled in a mixer with

0% of water
3% of 30% strength sodium chlorite solution
0.3% of Na m-benzene-disulfonate
0.1% of Na dodecylbenzene-sulfonate and
0.05% of chloroacetamide at 2-4 rpm for 2 hours. The hides are then stored at 25° C. After storage for 3 weeks, still no damage was detectable.

We claim:

1. A process for the short-term preservation of rawhides and skins with an alkali metal chlorite solution, which comprises treating the rawhides and skins with a 10-50% strength by weight solution of an alkali metal chlorite which additionally contains 0.5-10% by weight, based on the alkali metal chlorite solution, of a compound of the formula

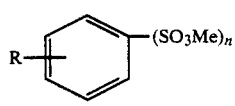

(I)

in which R denotes hydrogen or $C_1$–$C_{12}$-alkyl, Me denotes hydrogen or an alkali metal atom and n denotes 1 or 2.

2. The process as claimed in claim 1, wherein said compound of formula 1 is the sodium salt of 1,2-benzene-disulfonic acid.

3. The process as claimed in claim 1, wherein the rawhides and skins are treated with a said solution of an alkali metal chlorite which contains 0.1-5% by weight of a wetting and emulsifying agent in addition to said compound of formula 1.

4. The process as claimed in claim 3, wherein the amount of said wetting and emulsifying agent is 0.5-1% by weight.

5. The process as claimed in claim 1, wherein the rawhides and skins are also treated with a fungicide.

6. The process as claimed in claim 1, wherein the rawhides are treated by spraying or immersion.

7. The process as claimed in claim 1, wherein the rawhides or skins are additionally subjected to treatment with sodium chloride or brine.

8. A process for the inhibition of rot caused by microorganisms in rawhides and skins, which comprises treating the rawhides or skins with a solution comprising as a rot-preventing agent, 10 or 50% by weight, based on the weight of said solution, of an alkali metal chlorite, as a hydrotropic agent for improving the uniform penetration of said solution into the rawhide or skin, 0.5-10% by weight, based on the weight of said solution, of a compound of formula 1

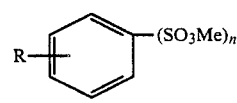

(I)

in which R denotes hydrogen or $C_1$–$C_{12}$ alkyl, Me denotes hydrogen or an alkali metal atom and n denotes 1 or 2.

9. The process as claimed in claim 8, wherein the compound of formula 1 is the sodium salt of 1,2-benzene-disulfonic acid.

10. The process as claimed in claim 8, wherein said solution contains, in addition to the compound of formula 1, a wetting and emulsifying agent or a fungicide.

11. The process as claimed in claim 8, wherein the rawhides or skins are treated by spraying them with an aqueous solution containing per liter of solution:

150-200 g of sodium chlorite,
15-30 g of a compound of formula 1,
1-5 g of wetting agent, and
0.1-0.5 g of a fungicide.

12. The process as claimed in claim 8, wherein the rawhides or skins are subjected to a bath treatment in an aqueous liquor containing:

10-30% by weight of a 10-50% strength sodium chlorite solution,
0.5-5% by weight of a compound of formula 1,
0.5-3% by weight of a wetting agent, and
0.05-0.5% by weight of a fungicide.

13. The process as claimed in claim 8, wherein the rawhides or skins are stored for at least 2 to 3 weeks and then processed into leather.

* * * * *